(12) United States Patent
Kendall et al.

(10) Patent No.: US 8,700,319 B2
(45) Date of Patent: Apr. 15, 2014

(54) METHOD OF MONITORING FITNESS LEVELS WITH A PERSONAL NAVIGATION DEVICE AND RELATED DEVICE THEREOF

(75) Inventors: Mark Steven Kendall, Auckland (NZ); Marcus Spranger, North Shore City (NZ); Mukesh Bhika, Auckland (NZ)

(73) Assignee: Mitac International Corp., Kuei-Shan Hsiang, Tao-Yuan Hsien (TW)

( * ) Notice: Subject to any disclaimer, the term of this patent is extended or adjusted under 35 U.S.C. 154(b) by 505 days.

(21) Appl. No.: 12/909,853

(22) Filed: Oct. 22, 2010

(65) Prior Publication Data

US 2012/0101723 A1    Apr. 26, 2012

(51) Int. Cl.
*G01C 21/00* (2006.01)
*G01C 21/04* (2006.01)

(52) U.S. Cl.
USPC ............................ 701/433; 701/448; 701/541

(58) Field of Classification Search
USPC .................... 701/433, 439, 448, 540, 541
See application file for complete search history.

(56) References Cited

U.S. PATENT DOCUMENTS

| | | | |
|---|---|---|---|
| 2003/0236614 A1* | 12/2003 | Yamakita et al. | 701/207 |
| 2006/0265122 A1* | 11/2006 | Chang et al. | 701/209 |
| 2008/0082254 A1* | 4/2008 | Huhtala et al. | 701/201 |
| 2008/0109158 A1* | 5/2008 | Huhtala et al. | 701/208 |
| 2009/0076765 A1 | 3/2009 | Kulach | |
| 2009/0248295 A1* | 10/2009 | Grewe | 701/202 |
| 2010/0245585 A1 | 9/2010 | Fisher | |
| 2010/0292914 A1* | 11/2010 | Vepsalainen | 701/200 |

FOREIGN PATENT DOCUMENTS

| | | |
|---|---|---|
| CN | 1226329 A | 8/1999 |
| CN | 1424861 A | 6/2003 |
| TW | 486576 | 5/2002 |
| TW | 200930008 | 7/2009 |

* cited by examiner

*Primary Examiner* — Jason Holloway
(74) *Attorney, Agent, or Firm* — Winston Hsu; Scott Margo

(57) ABSTRACT

A method of creating a customizable exercise route for a user of a personal navigation device is disclosed. The method includes providing routing instructions for a user along a first route, recording a first speed for a user traveling between a first point and a second point on the first route, providing routing instructions for a user along a second route, recording a second speed for a user traveling between a third point and a fourth point on the second route, comparing the first speed and the second speed to calculate a performance difference related to the first route and the second route, and notifying the user about the performance difference.

18 Claims, 6 Drawing Sheets

| Recorded database | Point 1 | Point 2 | Point 3 | Point 4 | Overall Speed |
|---|---|---|---|---|---|
| Time 1 (min) | 1:34 | 3:05 | 4:47 | 7:05 | 18.55 km/hr |
| Distance 1 (km) | 0.54 | 1.11 | 1.71 | 2.19 | |
| Time 2 (min) | 1:36 | 3:10 | 4:49 | 7:01 | 18.72 km/hr |
| Distance 2 (km) | 0.54 | 1.11 | 1.71 | 2.19 | |

FIG. 2

METHOD OF MONITORING FITNESS LEVELS WITH A PERSONAL NAVIGATION DEVICE AND RELATED DEVICE THEREOF

BACKGROUND OF THE INVENTION

1. Field of the Invention

The invention relates to a personal navigation device, and more particularly, to a personal navigation device that records fitness performance data about a user as the user exercises along a route for which the personal navigation device provides routing instructions.

2. Description of the Prior Art

Global Positioning System (GPS) based navigation devices are well known and are widely employed as in-car navigation devices. Common functions of a navigation device include providing a map database for generating routing instructions that are then shown on a display of the navigation device. These navigation devices are often mounted on or in the dashboard of a vehicle using a suction mount or other mounting means.

The term "navigation device" refers to a device that enables a user to navigate to a pre-defined destination. The device may have an internal system for receiving location data, such as a GPS receiver, or may merely be connectable to a receiver that can receive location data. The device may compute a route itself, or communicate with a remote server that computes the route and provides navigation information to the device, or a hybrid device in which the device itself and a remote server both play a role in the route computation process. Portable GPS navigation devices are not permanently integrated into a vehicle but instead are devices that can readily be mounted in or otherwise used inside a vehicle. Generally (but not necessarily), they are fully self-contained—i.e. include an internal GPS antenna, navigation software and maps and can hence plot and display a route to be taken.

As use of personal navigation devices becomes more widespread, pedestrians often carry personal navigation devices with them as they walk or exercise in the city or when they go hiking in the wilderness. The personal navigation device can provide routing instructions to the user if the user enters a destination location into the personal navigation device. Otherwise, if no set destination is entered, the personal navigation device can track the user's route for helping the user find his way back to the original starting point.

Unfortunately, the personal navigation device can only provide basic information that is useful to the user when the user is exercising. For example, the user is able to see the total distance traveled and may be able to see the elapsed time for traveling this distance. When the user is exercising, the user may wish to compare current fitness data, including time spent exercising and distance covered, to previous fitness data. However, the user is not able to conveniently see this data or compare performance metrics between different exercising sessions. Moreover, the personal navigation device does not provide any helpful information to the user regarding the user's progress on reaching fitness goals, such as completing a 10 kilometer run in less than 1 hour.

SUMMARY OF THE INVENTION

It is therefore one of the primary objectives of the claimed invention to provide a method of monitoring fitness levels with a personal navigation device for allowing users to conveniently view and track their fitness progress with the personal navigation device. Different fitness metrics can be created according to the distance traveled or the type of terrain crossed.

According to an exemplary embodiment of the claimed invention, a method of monitoring fitness levels with a personal navigation device is disclosed. The method includes utilizing the personal navigation device to provide routing instructions for a first route from a first point of the first route to a second point of the first route, measuring a first period of time needed for a user to travel from the first point to the second point and storing the measured first period of time in a memory of the personal navigation device, utilizing the personal navigation device to provide routing instructions for a second route from a third point of the second route to a fourth point of the second route, measuring a second period of time needed for the user to travel from the third point to the fourth point and storing the measured second period of time in the memory, calculating a first speed at which the user traveled between the first point and the second point according to a distance between the first point and second point and the measured first period of time, calculating a second speed at which the user traveled between the third point and the fourth point according to a distance between the third point and fourth point and the measured second period of time, comparing the first speed and the second speed to calculate a performance difference related to the first route and the second route, and notifying the user about the performance difference.

According to another exemplary embodiment of the claimed invention, a personal navigation device for monitoring fitness levels is disclosed. The personal navigation device includes routing software for utilizing the personal navigation device to provide routing instructions for a first route from a first point of the first route to a second point of the first route, and to provide routing instructions for a second route from a third point of the second route to a fourth point of the second route; a clock for measuring a first period of time needed for a user to travel from the first point to the second point, and for measuring a second period of time needed for the user to travel from the third point to the fourth point; a memory for storing the measured first period of time and the measured second period of time; a processor for controlling the personal navigation device, calculating a first speed at which the user traveled between the first point and the second point according to a distance between the first point and second point and the measured first period of time, calculating a second speed at which the user traveled between the third point and the fourth point according to a distance between the third point and fourth point and the measured second period of time, and comparing the first speed and the second speed to calculate a performance difference related to the first route and the second route; and a user interface for notifying the user about the performance difference.

It is an advantage that the personal navigation device can record key statistics for a user when the user is exercising such as distance traveled, time elapsed, difficulty level of the route, the terrain type for the route, and so on. The user can thus easily see his past fitness performance data, and make comparisons for determining if his performance is improving or not. If a user has a particular fitness goal in mind, the personal navigation device can also provide feedback to the user about his progress towards meeting the goal. The personal navigation device can help fitness professionals train for competitions as well as help average users keep fit.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 2 is a chart showing recorded fitness data according to the present invention.

FIG. 3 shows a graph plotting a user's speed with a distance of a route that the user is exercising on.

FIG. 4 shows a graph plotting a user's speed with a difficulty of a route that the user is exercising on.

DETAILED DESCRIPTION

Figure 1:
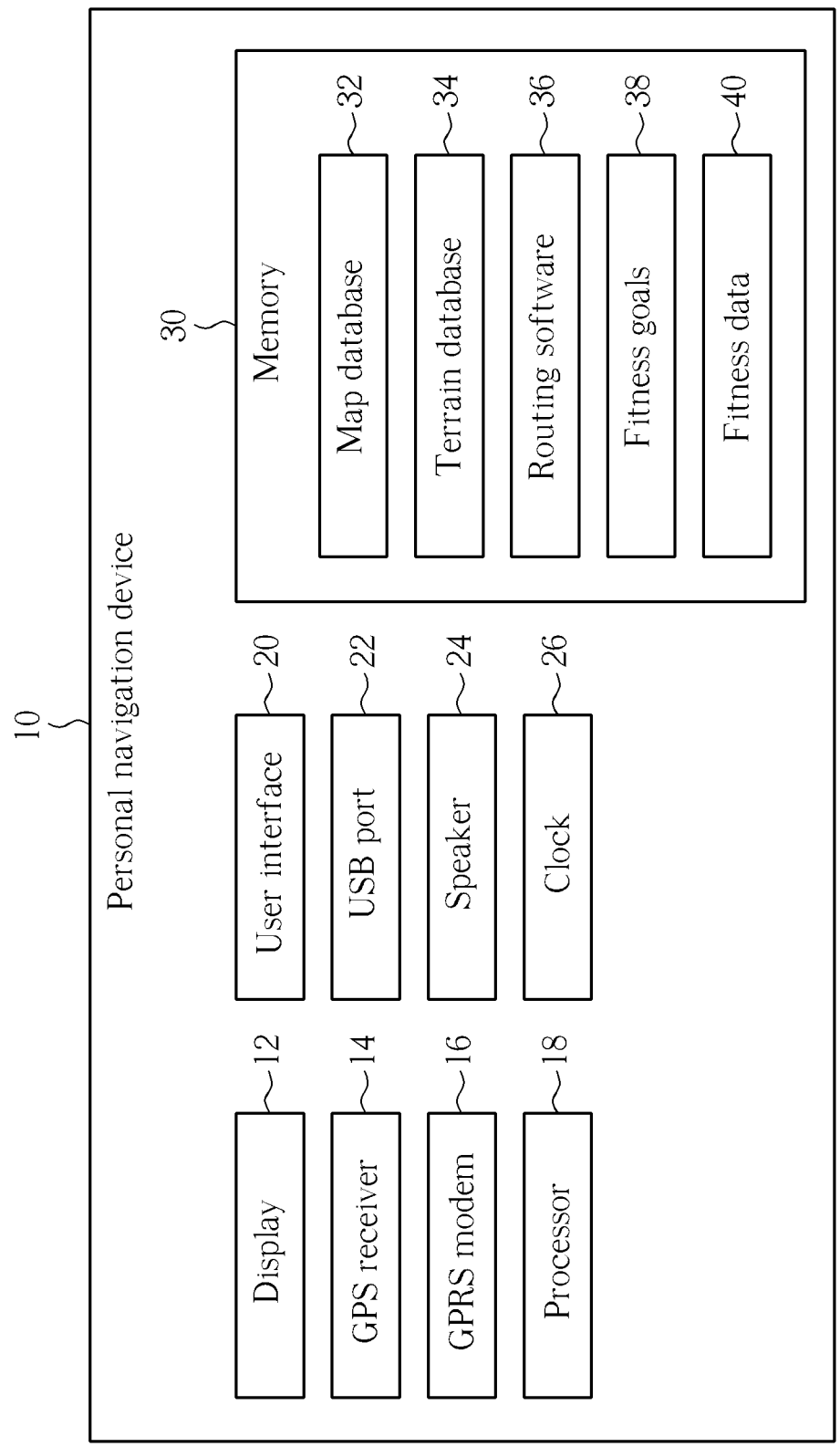
FIG. 1 is a block diagram of a personal navigation device according to the present invention.

Please refer to FIG. 1. FIG. 1 is a block diagram of a personal navigation device 10 according to the present invention. The personal navigation device 10 contains a display 12 which can be a touch sensitive display, a GPS receiver 14 for receiving the current coordinates of the personal navigation device 10, a General Packet Radio Service (GPRS) modem 16 for providing internet access, a processor 18 for controlling operation of the personal navigation device 10, a user interface 20, a Universal Serial Bus (USB) port 22 for allowing data to be exchanged with a computer, a speaker 24, a clock 26, and memory 30. The memory 30 is used to store a map database 32 containing map data and points of interest, a terrain database 34 containing terrain information of at least some of the areas covered by the map database 32, routing software 36, fitness goal data 38, as well as fitness data 40 recording data about the user's exercise efforts in the past. The user of the personal navigation device 10 can transfer fitness goal data 38 and fitness data 40 between a computer and the personal navigation device 10 using the USB port 22 or can transfer the data via the internet using the GPRS modem 16.

Please refer to FIG. 2. FIG. 2 is a chart 50 showing recorded fitness data 40 according to the present invention. The chart 50 shows time data, distance data, and speed data recorded when a user exercised on the same route two different times. The route may be generated by the routing software 36, which provides routing instructions for the user to follow the route. Data for time elapsed and distance covered at 4 different points along the route are recorded for both the user's first trip on the route and the user's second trip on the route. The route starts at point 0, and on the user's first trip along the route, the time elapsed when the user reaches point 1 is 1:34 minutes. Similarly, the time elapsed at point 2 is 3:05 minutes, the time elapsed at point 3 is 4:47 minutes, and the time elapsed at point 4 is 7:05 minutes. The overall speed for traveling from point 0 to point 4 on the user's first trip on the route is 18.55 km/hr.

As the user completes the first trip on the route, this time, distance, and speed data is recorded in the fitness data 40 section of memory 30. Depending on what information the user specified in the fitness goals 38, the user may be trying to steadily improve his fitness performance. As a result, the user can be given feedback by the personal navigation device 10 as the user exercises along the route the second time. On the user's second trip along the route, the time elapsed when the user reaches point 1 is 1:36 minutes, which is slightly slower then the user's first trip on the route. The personal navigation device 10 can inform the user about this situation and encourage the user to try harder. The time elapsed at point 2 is 3:10 minutes, which means that the user has lost even more time compared to the user's first trip along the route. At this time the personal navigation device 10 can give more feedback to the user, telling the user that he is falling behind the previous pace, and that the user needs to try much harder. Consequently, the user tries harder after point 2, and the time elapsed at point 3 is 4:49 minutes, which means the user is starting to make up time. The personal navigation device 10 can determine that while the user is speeding up, the user is still behind the pace set on the user's first trip along the route. Therefore, the personal navigation device 10 can provide encouraging feedback to the user and tell the user that he is doing better and he should keep trying. Finally, the time elapsed at point 4 is 7:01 minutes. Due to the feedback given by the personal navigation device 10 and due to the user's extra effort after point 2 on the route, the user was able to slightly improve upon his overall time on the user's second trip along the route. The overall speed for traveling from point 0 to point 4 on the user's second trip on the route is 18.72 km/hr.

Figure 6:
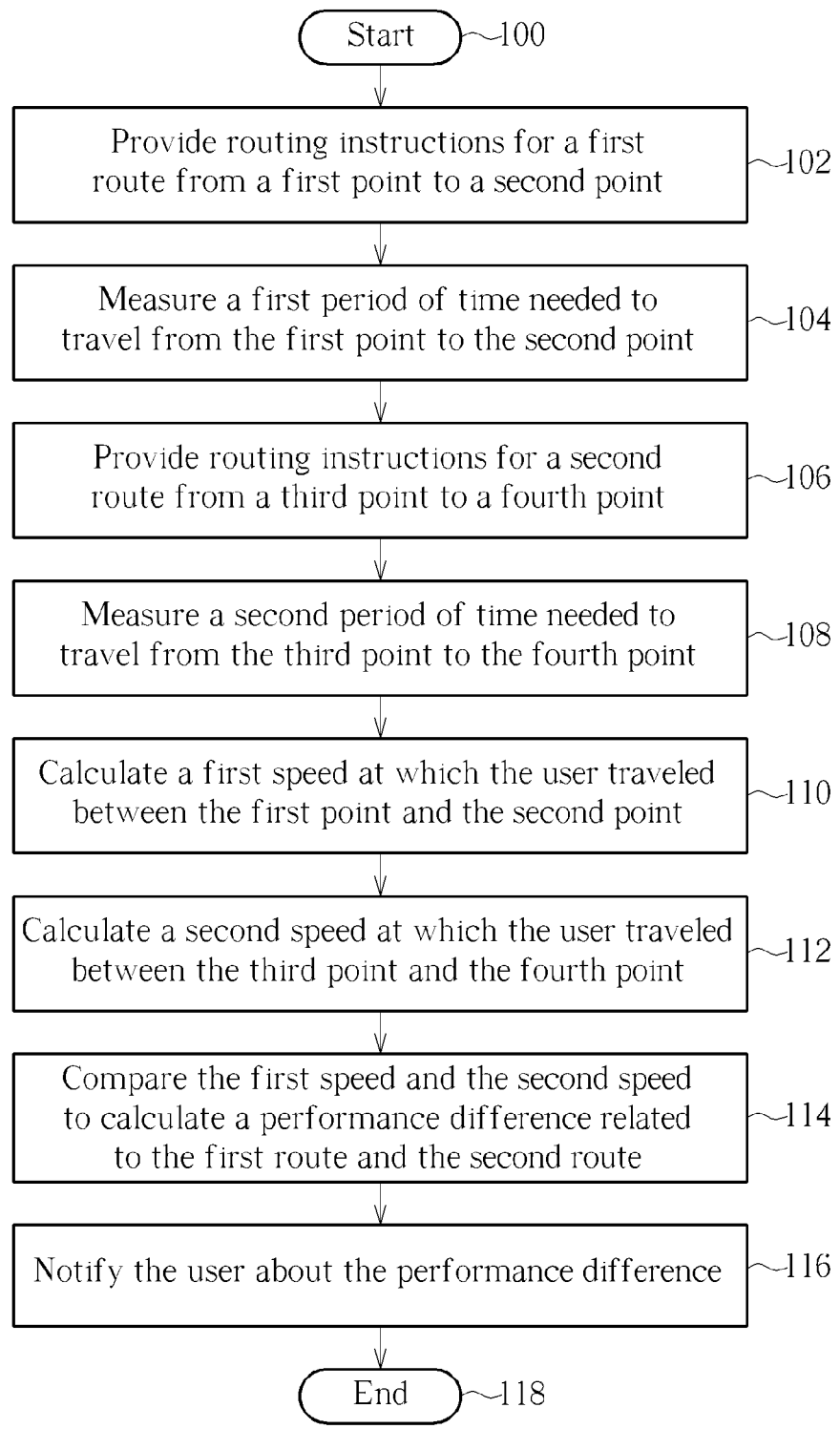
FIG. 6 is a flowchart illustrating a method of monitoring fitness levels with the personal navigation device according to the present invention.

Please refer to FIG. 6. FIG. 6 is a flowchart illustrating a method of monitoring fitness levels with the personal navigation device 10 according to the present invention. Steps contained in the flowchart will be explained below.

Step 100: Start.

Step 102: Execute the routing software 36 with the processor 18 to provide routing instructions for a first route from a first point of the first route to a second point of the first route. The user requests the personal navigation device 10 to create the first route by entering a desired terrain or difficulty level for the first route.

Step 104: Measure with the clock 26 a first period of time needed for a user to travel from the first point to the second point and store the measured first period of time in the memory 30 of the personal navigation device 10.

Step 106: Execute the routing software 36 with the processor 18 to provide routing instructions for a second route from a third point of the second route to a fourth point of the second route.

Step 108: Measure with the clock 26 a second period of time needed for the user to travel from the third point to the fourth point and store the measured second period of time in the memory 30.

Step 110: Calculate with the processor 18 a first speed at which the user traveled between the first point and the second point according to a distance between the first point and second point and the measured first period of time.

Step 112: Calculate with the processor 18 a second speed at which the user traveled between the third point and the fourth point according to a distance between the third point and fourth point and the measured second period of time.

Step 114: Compare with the processor 18 the first speed and the second speed to calculate a performance difference related to the first route and the second route.

Step 116: Notify the user about the performance difference.

Step 118: End.

In the example given above in the chart 50, the user traveled on the same route two different times. Although fitness level comparisons are easiest to make when the user travels on the same route multiple times, the user is not limited to traveling on the same route over and over again to gauge his fitness performance. Instead, the user can run along other routes and compare speeds at comparable distances for the different routes. The total distances of each route do not need to be the same either since the time and distance associated with a waypoint along the route can be used instead of relying only on the final destination point of the route for determining the user's speed along the route. In this way, the user can exercise on a number of different routes and still compare fitness data recorded along the different routes. For making comparisons between fitness data recorded on different routes as meaningful as possible, it is helpful if the total length and difficulty of the routes are as similar as possible, as will be explained below. Therefore, the user may choose to only compare fitness data when route distances are within a predetermined distance of each other.

It is well known that people often move at different paces when exercising on short routes than they do when exercising on long routes. A user often tries to move at a quick pace when exercising on a short route to give his body a better workout during a shorter amount of time. On the other hand, if the user is exercising on a long route, a slower pace is generally used so that the user does not wear himself out before the route is completed. Because of this, the personal navigation device 10 can classify fitness data according to route distance.

Figure 3:
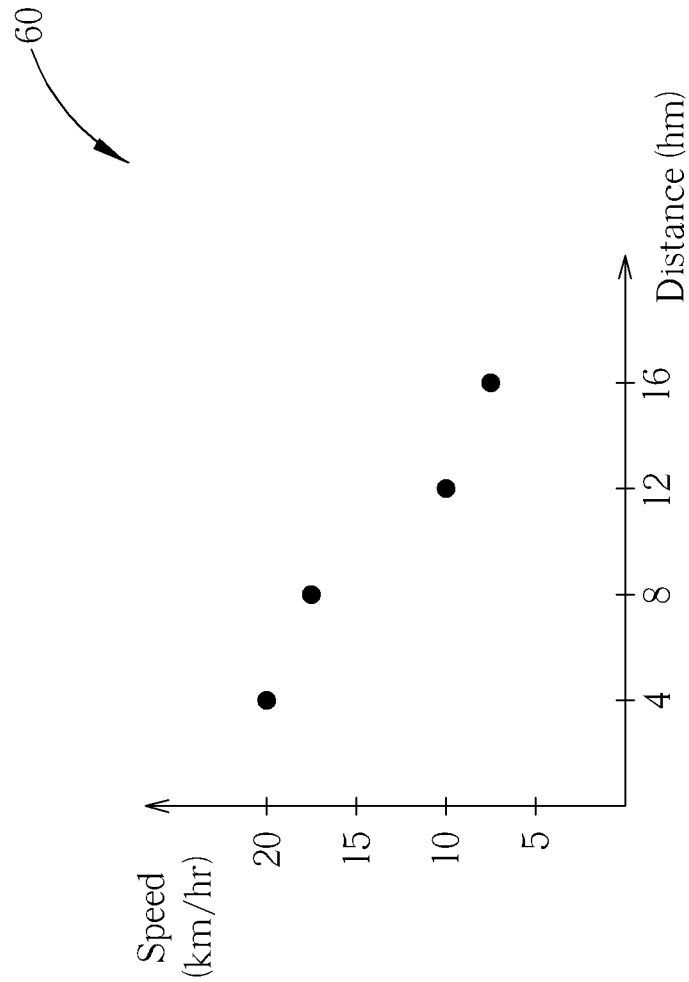

Please refer to FIG. 3. FIG. 3 shows a graph 60 plotting a user's speed with a distance of a route that the user is exercising on. In general, for shorter routes, the user can exercise at a much quicker speed than the user can for longer routes, as is illustrated in FIG. 3.

Unless two different routes are uniform in difficulty or in terrain type, it becomes harder to make a meaningful comparison between fitness data collected along the two different routes. Therefore, the personal navigation device 10 can make use of terrain data stored in the terrain database 34 for classifying fitness data according to terrain type or difficulty of the route. Terrain can be classified in a variety of different categories, such as routes with flat terrain, routes with hilly terrain, routes in urban areas, routes in a green belt area or a natural area, routes that have a significant number of stairs, or routes along a beach. Otherwise, the terrain can be classified according to a difficulty level, such as on a scale of 1 to 5.

Figure 4:
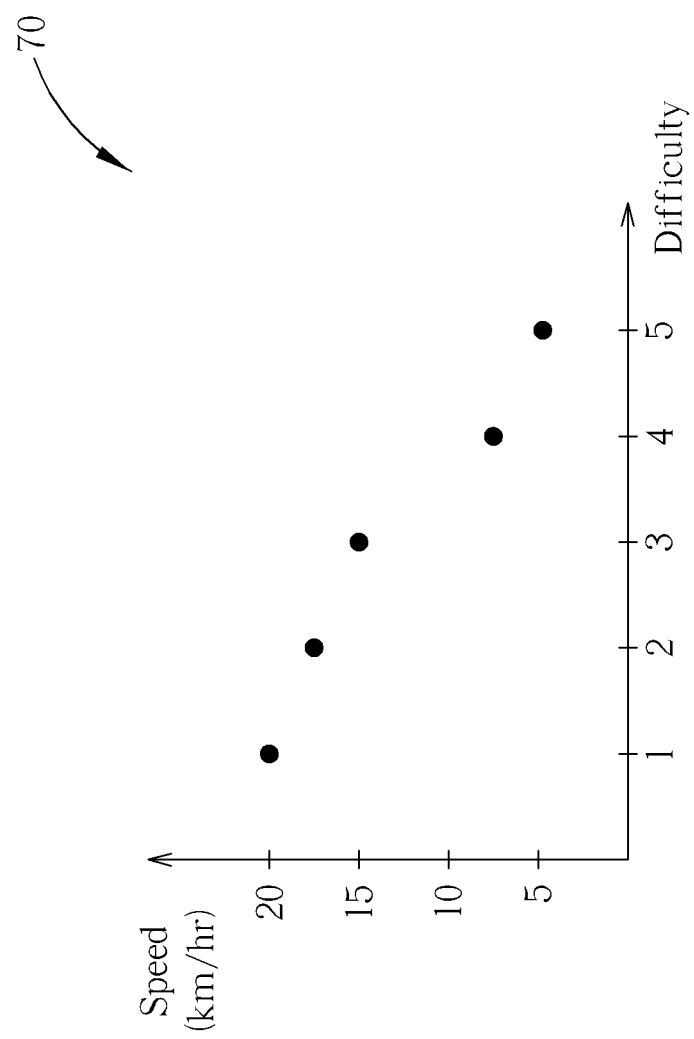

Please refer to FIG. 4. FIG. 4 shows a graph 70 plotting a user's speed with a difficulty of a route that the user is exercising on. In general, for easier routes, the user can exercise at a much quicker speed than the user can for more difficult routes, as is illustrated in FIG. 4.

All graphs can be depicted in a variety of different forms, depending on the number of variables involved. Both two-dimensional and three-dimensional graphs can be used, and the user can display the graphs on either the display 12 of the personal navigation device 10 or on a computer.

Once enough data has been recorded, the user can view the chart 50 and the graphs 60, 70 for seeing his performance at comparable distances, and different distances, and at different difficulty levels or terrain types. The user can then have a clear idea of his fitness level, and can more easily identify the areas that he would like to work on.

When the user is travelling in a place that the user is not familiar with, the user still should keep exercising in order to say in shape. Therefore, the user can enter desired exercise route parameters into the personal navigation device 10, and the routing software 36 will generate a suitable route for the user to follow. Even when the user is at home, the user can also request that the personal navigation device 10 generate a route in order to try a new route of a certain distance, to try a route with a different distance, to try a route with a different difficulty level, or to change other characteristics of the route.

When asking the personal navigation device 10 to create a route, the user could specify parameters such as a desired route distance and a desired difficulty level on a scale of 1 to 5. When selecting the route distance, the user can also select whether the starting point of the route should be the same as the ending point of the route. In other words, the route can be a one-way route if the starting and ending points are different, or can be a circular route if the starting and ending points are the same. When selecting the route difficulty level, the routing software 36 reads terrain data from the terrain database 34, which stores different terrains and their corresponding difficulty levels. The user can even specify that the route be created using two or more different difficulty levels. As an example, the user could choose to start the route with an initial section on easier terrain, follow that with a long middle section on difficult terrain, and finish with a final section on easier terrain.

Figure 5:
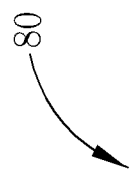
FIG. 5 shows a chart containing fitness goal data entered by the user.

The user may choose to enter specific goal data into the fitness goals 38 section of memory 30. Please refer to FIG. 5. FIG. 5 shows a chart 80 containing fitness goal data entered by the user. The chart 80 contains time periods in which a user would like to complete routes of various distances. For example, the user may have a goal of finishing a 5 km run in 25 minutes, a 10 km run in 60 minutes, and a 15 km run in 100 minutes. Once the user has entered goal data into the fitness goals 38 section of memory 30, the personal navigation device 10 can provide better feedback and training support to the user for helping the user to achieve his goals. After the user enters fitness goals, the personal navigation device 10 can suggest a training plan or a fitness program for helping the user to slowly build up to achieving this goal. In addition, every time the user exercises on an exercise route, the personal navigation device 10 can provide feedback or comparison results that show how the user is doing compared to past results with various corresponding levels of difficulty or distances of the exercise routes.

In summary, the personal navigation device records fitness statistics for a user when the user is exercising such as distance traveled, time elapsed, difficulty level of the route, the terrain type for the route, and so on. The user can then view charts or graphs for viewing his fitness performance, and make comparisons with previously stored data to determine if his performance is improving or not. If a user has a particular fitness goal in mind, the personal navigation device can also provide feedback to the user about his progress towards meeting the goal.

Those skilled in the art will readily observe that numerous modifications and alterations of the device and method may be made while retaining the teachings of the invention.

What is claimed is:

1. A method of monitoring fitness levels with a personal navigation device, the method comprising:

receiving, from a user, selection of desired exercise route parameters including a desired terrain type or difficulty level;

searching a terrain database stored locally on the personal navigation device which locates paths with the desired exercise route parameters including the desired terrain type or difficulty level selected by the user;

creating a first route with a routing software of the personal navigation device based on the desired exercise route parameters including the desired terrain type or difficulty level selected by the user, and using paths located from the terrain database;

executing the routing software with a processor of the personal navigation device which provides routing instructions for the user to follow for the first route from a first point of the first route to a second point of the first route;

measuring a first period of time needed for the user to travel from the first point to the second point and storing the measured first period of time in a memory of the personal navigation device;

executing routing software with the processor which provides routing instructions for the user to follow for a second route from a third point of the second route to a fourth point of the second route;

measuring a second period of time needed for the user to travel from the third point to the fourth point and storing the measured second period of time in the memory;

calculating, with the processor, a first speed at which the user traveled between the first point and the second point according to a distance between the first point and second point and the measured first period of time;

calculating, with the processor, a second speed at which the user traveled between the third point and the fourth point according to a distance between the third point and fourth point and the measured second period of time;

comparing, with the processor, the first speed and the second speed to calculate a performance difference related to the first route and the second route; and notifying the user about the performance difference.

2. The method of claim 1, wherein the third point is the same as the first point and the fourth point is the same as the second point.

3. The method of claim 1, wherein the first point is a starting point of the first route and the second point is a destination point of the first route.

4. The method of claim 1, wherein the first point and the second point are waypoints along the first route.

5. The method of claim 1, wherein distance, terrain, or route difficulty between the first point and the second point is similar to that between the third point and the fourth point.

6. The method of claim 1, wherein the user requests the personal navigation device to create the first route by entering a desired distance for the first route.

7. The method of claim 6, wherein a starting point of the first route is requested to be the same as an ending point of the first route.

8. The method of claim 1, wherein notifying the user about the performance difference comprises displaying speed or time information versus a corresponding distance traveled or terrain information.

9. The method of claim 1, further comprising recording fitness goals set by the user and giving feedback to the user when the user is exercising along a route about the user's current progress and how this compares with the fitness goals set by the user.

10. A personal navigation device for monitoring fitness levels, comprising:

a user interface configured to receive, from a user, selection of desired exercise route parameters including a desired terrain type or difficulty level;

a terrain database containing a plurality of paths and corresponding terrain or difficulty level data;

routing software which searches the terrain database and locates paths with the desired exercise route parameters including the desired terrain type or difficulty level selected by the user and creating a first route based on the desired exercise route parameters including the desired terrain type or difficulty level selected by the user, and using paths located from the terrain database, the routing software utilizing the personal navigation device to provide routing instructions for the user to follow for the first route from a first point of the first route to a second point of the first route, and to provide routing instructions for the user to follow for a second route from a third point of the second route to a fourth point of the second route;

a clock configured to measure a first period of time needed for the user to travel from the first point to the second point, and measure a second period of time needed for the user to travel from the third point to the fourth point;

a memory configured to store the measured first period of time and the measured second period of time; and a processor configured to control the personal navigation device, calculate a first speed at which the user traveled between the first point and the second point according to a distance between the first point and second point and the measured first period of time, calculate a second speed at which the user traveled between the third point and the fourth point according to a distance between the third point and fourth point and the measured second period of time, and compare the first speed and the second speed to calculate a performance difference related to the first route and the second route;

wherein the user interface notifies the user about the performance difference.

11. The personal navigation device of claim 10, wherein the third point is the same as the first point and the fourth point is the same as the second point.

12. The personal navigation device of claim 10, wherein the first point is a starting point of the first route and the second point is a destination point of the first route.

13. The personal navigation device of claim 10, wherein the first point and the second point are waypoints along the first route.

14. The personal navigation device of claim 10, wherein distance, terrain, or route difficulty between the first point and the second point is similar to that between the third point and the fourth point.

15. The personal navigation device of claim 10, wherein the user requests the routing software to create the first route by entering a desired distance for the first route.

16. The personal navigation device of claim 15, wherein a starting point of the first route is requested to be the same as an ending point of the first route.

17. The personal navigation device of claim 10, wherein the user interface notifies the user about the performance difference by displaying speed or time information versus a corresponding distance traveled or terrain information.

18. The personal navigation device of claim 10, wherein the user interface allows the user to record fitness goals in the memory, and the processor gives feedback to the user when the user is exercising along a route about the user's current progress and how this compares with the fitness goals recorded by the user.

* * * * *